US00PP25305P3

(12) United States Plant Patent
Kardos

(10) Patent No.: US PP25,305 P3
(45) Date of Patent: Feb. 24, 2015

(54) ***ABELIA* PLANT NAMED 'PIIAB-II'**

(50) Latin Name: *Abelia×grandiflora*
Varietal Denomination: PIIAB-II

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 132 days.

(21) Appl. No.: 13/815,704

(22) Filed: Mar. 14, 2013

(65) Prior Publication Data

US 2014/0283248 P1 Sep. 18, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Lathrop & Gage LLP

(57) ABSTRACT

A new and distinct cultivar of *Abelia* plant named 'PIIAB-II', characterized by its compact, mounding to spreading growth habit, bronze new growth that turns to yellow-green and finally matures to green, semi-evergreen foliage that does not photobleach or burn in full sun like some other yellow foliage cultivars, early and abundant flowering during the growing season, light pink flower buds that open to white flowers with persistent pink sepals.

4 Drawing Sheets

Genus and species of plant claimed: *Abelia×grandiflora.*
Variety denomination: 'PIIAB-II'.

BACKGROUND OF THE INVENTION

The present invention relates to a new and distinct cultivar of *Abelia* plant, botanically known as *Abelia×grandiflora,* commonly known as *Abelia,* and hereinafter referred to by the cultivar name 'PIIAB-II'. 'PIIAB-II' is grown primarily as an ornamental for landscape use and for use as a potted plant.

'PIIAB-II' originated in 2008 from open-pollinated seed of *Abelia* 'PIIAB-I' (unpatented) as part of a breeding program in Watkinsville, Ga. The cultivar 'PIIAB-II' originated and was selected by the inventor in a cultivated environment in Watkinsville, Ga. from the progeny of this open-pollination by continued evaluation for growth habit and foliage and flower characteristics.

Asexual reproduction of 'PIIAB-II' by stem cuttings in Watkinsville, Ga. since 2009 has shown that all the unique features of this new *Abelia,* as herein described, are stable and reproduced true-to-type through successive generations of such asexual propagation.

SUMMARY OF THE INVENTION

Plants of the new cultivar 'PIIAB-II' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIAB-II'. These characteristics in combination distinguish 'PIIAB-II' as a new and distinct cultivar: 1. Compact, mounding to spreading growth habit; 2. Bronze new growth that turns to yellow-green and finally matures to green; 3. Semi-evergreen foliage that does not photobleach or burn in full sun like some other yellow foliage cultivars; 4. Early and abundant flowering during the growing season; 5. Light pink flower buds that open to white flowers with persistent pink sepals.

Plants of 'PIIAB-II' differ from plants of the parent, 'PIIAB-I', primarily in growth habit and sepal color. Plants of 'PIIAB-II' have a compact, mounding to spreading growth habit and pink sepals, whereas plants of 'PIIAB-I' have a larger, upright to rounded growth habit and burgundy-rose sepals.

Plants of 'PIIAB-II' can be compared to plants of 'Canyon Creek' (unpatented) but differ in growth habit, foliage color, and flower color. Plants of 'PIIAB-II' have a compact, mounding to spreading growth habit, foliage that does not photobleach or burn, and white flowers, whereas plants of 'Canyon Creek' have a larger, rounded to upright growth habit, foliage that is susceptible to photobleaching or burning, and pink flowers.

BRIEF DESCRIPTION OF THE DRAWINGS

The accompanying color photographs illustrate the flower and foliage characteristics and the overall appearance of 'PIIAB-II', showing the colors as true as it is reasonably possible to obtain in color reproductions of this type. Colors in the photographs may differ slightly from the color values cited in the detailed botanical description which accurately describe the colors of the new *Abelia.*

DETAILED DESCRIPTION

Figure 1:
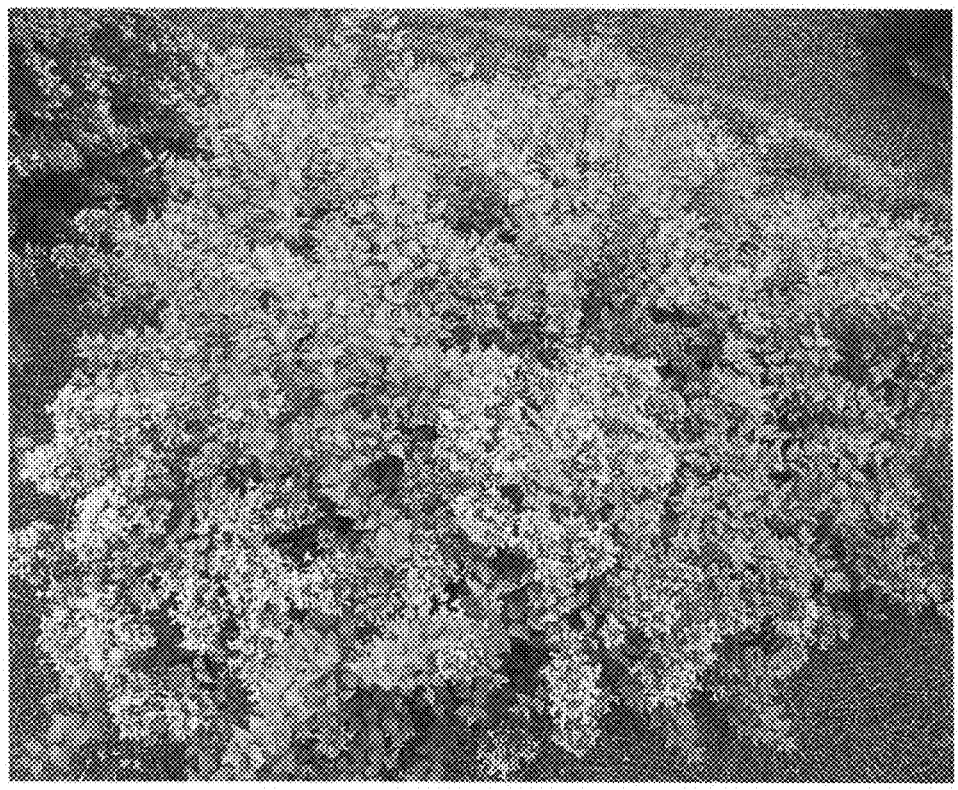
FIG. 1 illustrates the new growth, intermediate foliage color, flowers, and overall appearance of a plant of 'PIIAB-II' planted in the ground.
Figure 2:
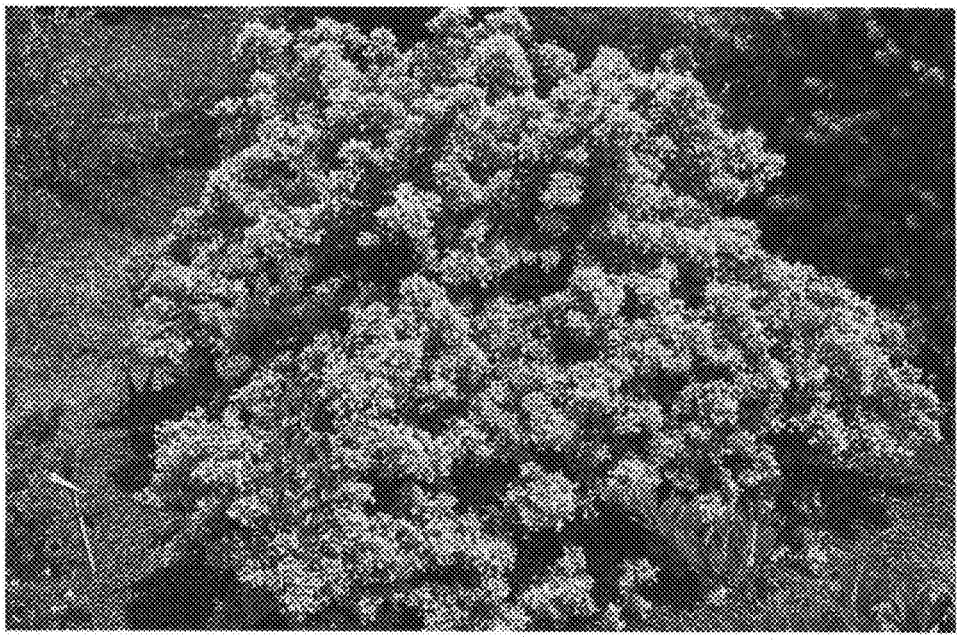
FIG. 2 illustrates the mature foliage, flowers, and overall appearance of a plant of 'PIIAB-II' planted in the ground.
Figure 3:
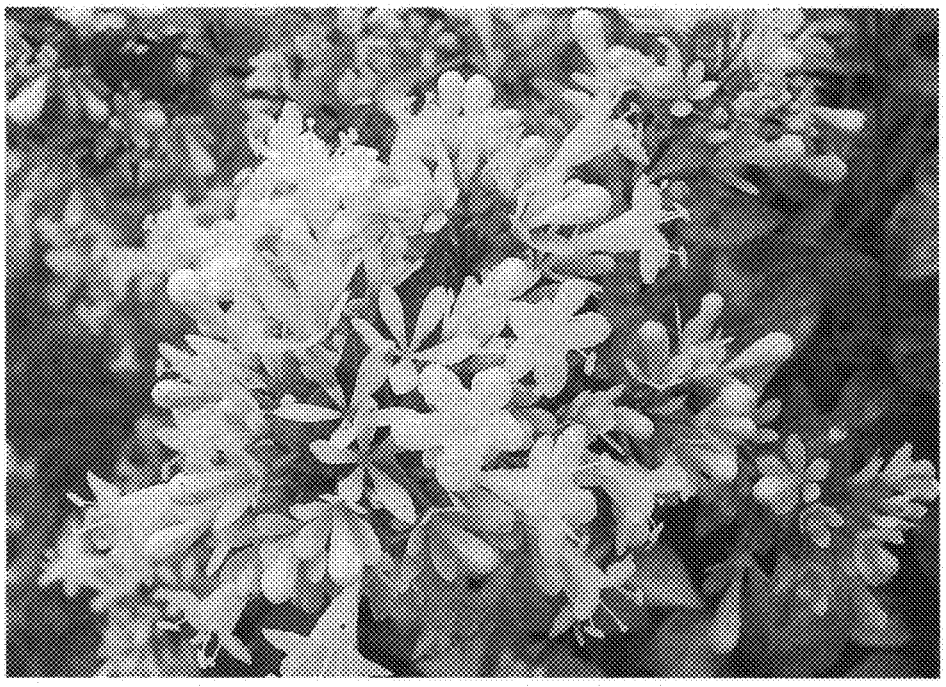
FIG. 3 illustrates a close-up view of the flowers of 'PIIAB-II'.
Figure 4:
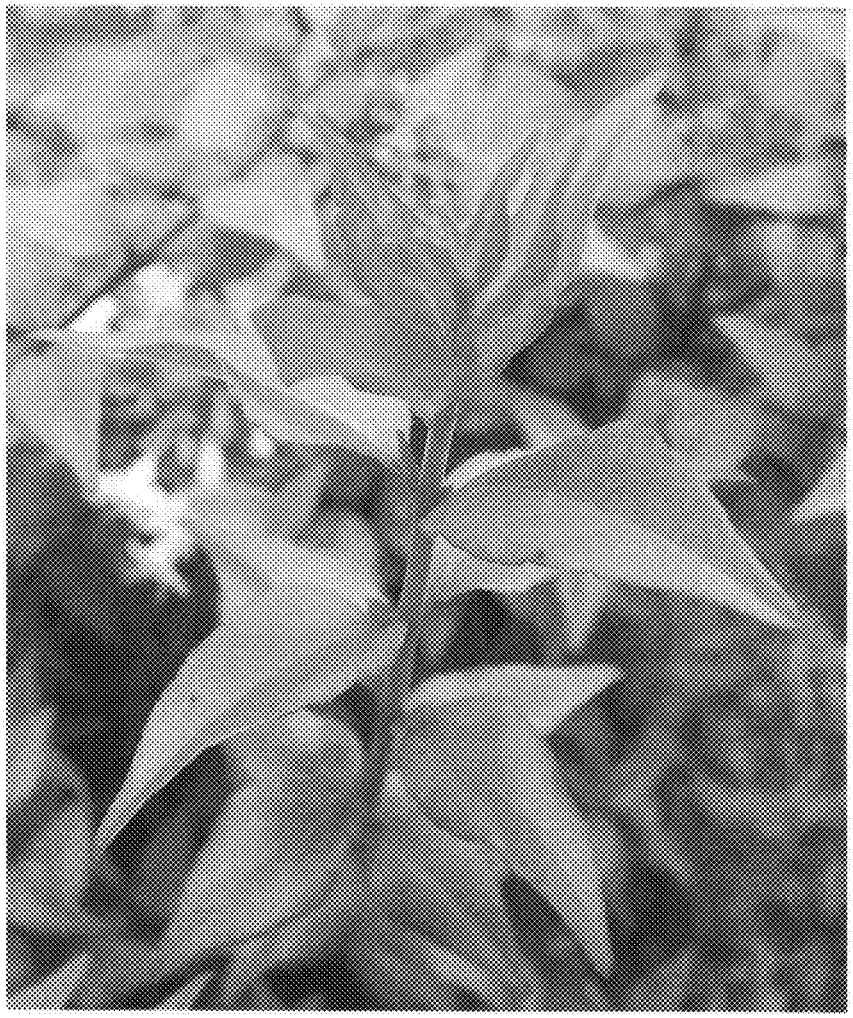
FIG. 4 illustrates a close-up view of the new growth of 'PIIAB-II'.

In the following description, color references are made to The Royal Horticultural Society Colour Chart, 2007 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Abelia×grandiflora,* cultivar 'PIIAB-II'.

Parentage:

*Female, or seed, parent.*—*Abelia×grandiflora* 'PIIAB-I' (unpatented).

*Male, or pollen parent.*—Unknown (open-pollinated).

Propagation: Terminal cuttings.

Time to initiate roots, summer: About 21 days at 32° C.

Plant description: Small, semi-evergreen, flowering shrub; compact, mounding to spreading growth habit. Freely branching; pruning enhances lateral branch development.

*Root description.*—Numerous, fine, fibrous and well-branched.

*Plant size.*—The original plant, now about four and a half years old in the ground, is about 81 cm high from the soil level to the top of the inflorescences and about 165 cm wide. First year stems have a diameter of about 2 mm. Shape: round. Pubescence: finely pubescent. Second year and older stems have a diameter of about 3 mm or more. Shape: round.

*Trunk diameter.*—1 cm at the soil line. Exfoliating bark, color 200B, peels off to reveal the main trunk underneath, color 199C.

*Internode length.*—About 1.4 cm.

*Strength.*—Flexible when young, easily broken once mature.

*First year stem color* (*young*).—N34D. Color (woody): 200B.

*Second year and older stem color.*—200B.

*Bark.*—Exfoliates in strips beginning on second year and older stems.

Vegetative buds: Opposite in arrangement, ovoid, 2 pairs of bud scales, finely pubescent.

*Color.*—173B.

*Size.*—About 1.5 mm in length and 1 mm in width.

Foliage description:

*Arrangement.*—Opposite, simple.

*Length.*—About 3.7 cm.

*Width.*—About 1.4 cm.

*Shape.*—Ovate.

*Apex.*—Acute.

*Base.*—Rounded to cuneate.

*Margin.*—Entire to dentate.

*Texture* (*upper surface*).—Lustrous, finely pubescent.

*Texture* (*lower surface*).—Matte, finely pubescent.

*Venation pattern.*—Pinnate.

*Venation color of emerging foliage* (*upper surface*).—1A.

*Venation color of emerging foliage* (*lower surface*).—151B.

*Venation color of intermediate foliage* (*upper surface*).—N144A.

*Venation color of intermediate foliage* (*lower surface*).—144D.

*Venation color of mature foliage* (*upper surface*).—146A.

*Venation color of mature foliage* (*lower surface*).—147C.

*Color in developing foliage* (*upper surface*).—169C.

*Color in developing foliage* (*lower surface*).—N163D.

*Color in intermediate foliage* (*upper surface*).—N144A.

*Color in intermediate foliage* (*lower surface*).—144D.

*Color in mature foliage* (*upper surface*).—146A.

*Color in mature foliage* (*lower surface*).—147C.

*Petiole length.*—About 3 mm.

*Petiole diameter.*—About 1 mm.

*Petiole color on mature foliage* (*upper and lower surfaces*).—146B.

*Pubescence.*—Finely pubescent.

Flower description: Flowers on new growth of the season, usually from about May to June and sporadically until frost in Watkinsville, Ga. An inflorescence is showy for up to about five months due to the presence of persistent, colourful sepals. Individual flowers last about a week and are self-cleaning. Flowers have a faint, pleasant fragrance.

*Inflorescence type.*—Terminal and axillary panicles containing campanulate flowers.

*Inflorescence height.*—About 5.5 cm.

*Inflorescence width.*—About 6.5 cm.

*Peduncle.*—About 5 cm in length, about 2 mm in diameter, color is 178C, and finely pubescent.

*Individual flowers.*—About 2 cm in height and 1.4 cm in diameter.

*Flower buds.*—Length: about 2.2 mm; Diameter: about 4 mm; Color: 159C.

*Pedicels.*—About 5 mm in length, 178C in color, and finely pubescent.

*Calyx.*—Consisting of a single whorl of 5 sepals, each about 6 mm in length, about 2 mm in width, and fused at the base, 38D in color, and no pubescence.

Petals:

*Arrangement/appearance.*—Single whorl of 5 fused petals per flower.

*Lobe length.*—About 5 mm.

*Lobe width.*—About 4 mm.

*Petal shape.*—Roughly spatulate.

*Petal apex.*—Obtuse.

*Petal margin.*—Entire.

*Petal texture* (*upper and lower surfaces*).—Smooth, with sparse fine pubescence.

*Petal color.*—Upper and lower surfaces are NN155D.

Stamens:

*Quantity/arrangement.*—5 stamens per flower, about 5 mm in length.

*Filaments.*—About 4 mm in length and about 0.5 mm in width, and NN155D in color.

*Anthers.*—About 2.5 mm in length and 1 mm in width, and NN155A in color.

*Pollen.*—Produced in small quantities and is NN155A in color.

Pistils:

*Quantity.*—One pistil per flower.

*Pubescence.*—None.

*Pistil length.*—About 2.5 cm in length.

*Stigma*.—Round, about 1 mm in diameter, and 155B in color.

*Style*.—About 1.7 cm in length, about 1 mm in width, and NN155D in color.

*Ovary*.—One inferior ovary per flower, about 7 mm in length, about 1 mm in width, and 173B in color.

Fruit:

*Type/appearance*.—One-seeded, leathery, tubular achene.

*Length*.—About 7 mm.

*Width*.—About 2 mm.

*Mature color*.—177A.

Disease/pest resistance: Plants of the new *Abelia* have not been shown to be resistant to pathogens and pests common to *Abelia*.

I claim:

1. A new and distinct *Abelia* plant named 'PIIAB-II', as illustrated and described herein.

* * * * *